United States Patent [19]

Prosen

[11] 4,046,561

[45] Sept. 6, 1977

[54] DENTAL ALLOY OF USE IN THE ADHESION OF PORCELAIN

[75] Inventor: Emil M. Prosen, Bala-Cynwyd, Pa.

[73] Assignee: Neoloy Products, Inc., Posen, Ill.

[21] Appl. No.: 719,367

[22] Filed: Sept. 1, 1976

[51] Int. Cl.² ............................................. C22C 5/04
[52] U.S. Cl. ................................................. 75/172 R
[58] Field of Search ..................................... 75/172 R

[56] References Cited

U.S. PATENT DOCUMENTS

| | | | |
|---|---|---|---|
| 2,890,114 | 6/1959 | Ruthardt et al. | 75/172 R |
| 3,276,113 | 10/1966 | Metcalfe | 75/172 R X |
| 3,819,366 | 6/1974 | Katz | 75/172 R |
| 3,928,913 | 12/1975 | Schaffer | 75/172 R X |
| 3,929,474 | 12/1975 | Ingersoll | 75/172 G |

FOREIGN PATENT DOCUMENTS

| | | | |
|---|---|---|---|
| 454,019 | 1/1949 | Canada | 75/172 R |
| 2,043,492 | 3/1972 | Germany | 75/172 R |

*Primary Examiner*—L. Dewayne Rutledge
*Assistant Examiner*—E. L. Weise
*Attorney, Agent, or Firm*—Cooper, Dunham, Clark, Griffin & Moran

[57] ABSTRACT

The present invention provides a precious metal alloy consisting essentially of palladium, from 1-3% of boron, and up to 3% of molybdenum. In its preferred form the boron content is approximately 1.3%, the molybdenum content is approximately 2%, and the alloy has a melting point of approximately 2600° F. To reduce the melting point of this alloy to approximately 2500° F. for low-fusing porcelain application, nickel or gallium is added in an amount of slightly less than 5%.

5 Claims, No Drawings

DENTAL ALLOY OF USE IN THE ADHESION OF PORCELAIN

The present invention relates to a precious metal alloy especially adapted for use in the dental field for the preparation of caps, crowns, inlays, partial appliances and other dental prostheses to which it is desired to apply a porcelain or other like ceramic surface. In its broadest aspects the alloy of the present invention not only has specific use in the dental field, but has general use in the field of jewelry and like areas. The most important advantage of the alloy of the present invention, however, is in the dental field in that it provides an alloy to which a low-fusing porcelain can be adhered by fusion, with none of the disadvantages of heretofore known alloys.

BACKGROUND OF THE INVENTION

In the dental field one of the most sought after alloys is one to which porcelain can be applied by fusion and which will have complete adhesion throughout the temperature range and other conditions to which the alloy and porcelain will be subjected during processing and use.

Among the many well recognized problems in applying low-fusing porcelain to a dental alloy to provide exterior porcelain surfaces thereon is that the coefficient of expansion of the alloy and the porcelain should be completely matched and compatible so that on cooling the porcelain will not check, crack or separate from the metal alloy.

Also, with precious metal alloys such as alloys of yellow gold, platinum and palladium in fractional percentages it has not been possible to obtain a true bond between the alloy and the porcelain. Hence various alternatives have been suggested for adding to a precious metal alloy other metal elements which at porcelain fusing temperatures would provide on the surface of such alloy bonding oxides.

Among the metals proposed to be added to provide such bonding oxides were copper, cobalt and silver. It has been found, however, that the oxides of copper, cobalt and silver are undesirable for dental purposes from the standpoint of esthetics for the reasons that copper oxide turns porcelain green; cobalt oxide turns porcelain blue; and silver oxide turns porcelain yellow.

Another disadvantage of a yellow gold precious metal alloy from the standpoint of application of low-fusing porcelain is that yellow gold melts at 1940° F. and low-fusing porcelain fuses at 1800° F. As a consequence the temperature differential between the yellow gold and the fusing porcelain was too close and the yellow gold was unable to maintain its rigidity during the fusing operation.

In order to strengthen yellow gold and to improve its rigidity for the purpose of fusing porcelain thereto, it has heretofore been proposed to add platinum and palladium to provide a precious metal alloy. In order to maintain the yellow color of gold, however, it has been found that the white metals (platinum and palladium) should not exceed 10% of the alloy composition.

In view of the high cost of gold and its high specific gravity, which approximates 19, efforts have been made to employ palladium as a substitute for yellow gold. Even though palladium has the white color, it was thought desirable to employ palladium in dental alloys because of the other physical and workability characteristics of such alloy. Also, as a substitute for yellow gold it was found that palladium could be combined with silver, nickel and other elements to provide an alloy suitable for porcelain application which would have the high temperature melting point necessary and would also have the rigidity of an alloy structure necessary for porcelain application.

Among the prior art patents generally relating to the subject matter of this invention are:

U.S. Pat. No. 3,819,366 in the name of Michel Katz and entitled "Dental Alloy", wherein the precious alloy for use in dental frames on which ceramic coverings or acrylic coverings are formed consists of 8-76 weight percent palladium and 0.2-18 weight percent indium, 0-15 weight percent zinc, and other trace metals in amounts no greater than 1¾ weight percent.

Schaffer U.S. Pat. No. 3,928,913, entitled "Palladium Alloy for Ceramic Bonding" discloses a dental casting alloy consisting essentially of 40-60 percent of a precious metal component selected from the group consisting of palladium and mixtures of palladium and platinum wherein the platinum is in the amount of up to 12 percent of the alloy but not in excess of 25 percent of the palladium content; 20-59 percent of a non-precious metal component selected from the group consisting of 20-50 percent cobalt and mixtures of 20-50 percent cobalt and up to 25 percent nickel wherein the nickel content does not exceed the cobalt content; and a modifier selected from the group consisting of 1-8 percent indium, 1-3 percent tin and 1-8 percent of mixtures of tin and indium wherein the tin does not exceed 3 percent.

U.S. Pat. No. 3,929,474, dated Dec. 30, 1975 for "Tarnish Resistant Silver Based Dental Casting Alloy Capable of Bonding to Porcelain" in the name of Clyde E. Ingersoll, which discloses and claims an alloy to which porcelain may be directly fused, — the alloy composition comprising: 35-60% Pd, at least about 0.5-7% of one member of the group consisting of Cr, Fe, In and Sn and from about to 0 to 5% of the group consisting of Si, Ni, Co, Ta, and Ti, and the rest Ag.

For completeness of disclosure it should be noted that Schaffer U.S. Pat. No. 3,928,913 also mentions molybdenum in the amount of 2-8 percent as a desirable additive and that nickel in the amount of 10-20 percent desirably comprises a protion of the non-precious metal component.

SUMMARY OF THE INVENTION

In my experimental work looking toward a precious metal dental alloy which would meet all of the pre-existing requirements for adhesion of low-fusing porcelain, I decided to concentrate on palladium as a substitute for yellow gold and platinum. In my early experiments with palladium I used boron as part of the alloy and found that with boron in small percentages such as 2%, the alloy of palladium and boron melted at about 2600° F. and formed a very desirable alloy. I also found, however, that when the alloy thus prepared was brought up to a temperature of 1800° F. for adhesion of low-fusing porcelain the alloy became very brittle and had no stability. Thus as part of my experimentation I have found that palladium when alloyed with boron in small percentages such as 2% would melt at 2600° F. to form a very desirable alloy, — but does not lend itself to the application of low-fusing porcelain when it is subsequently brought to the temperature of 1800° F. for adhesion of such low-fusing porcelain for the reason that the alloy becomes very brittle at elevated temperatures and has no stability.

I then embarked on further experimentation in order to eliminate, if possible, the undesirable brittleness of the palladium-boron alloy when fusing with porcelain at 1800° F. By repeated experimentation and using almost every metallic element in the periodic table, I finally discovered that with the addition of about 3% molybdenum to this alloy during fusion of porcelain became completely stable, and in final form exhibited complete resistance to separation of the porcelain from the alloy under the impact of the most severe tests. I also found that with the application of heavy blows on impact tests the porcelain did crack and chip away, but the porcelain still was retained on the surface of the alloy because the adhesion of the porcelain to the alloy was stronger than the porcelain itself. Finally, I found that in order to remove all of the porcelain from the alloy it was necessary either to grind it off or to dissolve it in hydrofluoric acid.

To summarize my experimentation results I would say that a precious metal alloy consisting chiefly of palladium and containing about 1.3% boron and 2% molybdenum constitutes a dental alloy which has a melting point of approximately 2600° F. which is capable of being fused to low-fusing porcelain at about 1800° F. and which has the requisite rigidity to prevent checking of the porcelain under fusing and other use conditions to which the dental restoration is subjected.

While the foregoing alloy consisting of palladium, boron and molybdenum in the recited preferred percentages gives rise to a very desirable dental alloy, its only drawback (it it has a drawback) is that it has a melting point of approximately 2600° F. From a practical standpoint it is much easier to work with an alloy which has a melting point of approximately 2500° F.

In further experimentation I found that by adding about 5% nickel to the alloy the melting temperature of the alloy would drop by 100° F. or to 2500° F. I also found that the upper limit of nickel to be added is 5% for the reason that there is a loss of fusion between porcelain and the metal alloy when the alloy contains more than 5% nickel. Hence, it is recommended that the nickel content be no more than 5% and preferably slightly less. As a substitute for nickel, gallium may be used up to 5% maximum.

As earlier mentioned, many of the metal alloys heretofore known for application of porcelain by fusion depend upon a metal oxide on the surface of the metal to promote the fusion and adhesion. In the present alloy the porcelain fusion does not depend upon any oxide of metal. There is no oxide in the alloy consisting of palladium, boron and molybdenum in the recited percentages and the mere addition of 5% maximum of nickel or gallium does not form an oxide strong enough to overcome the influence of the non-oxidizing palladium and boron Among the unusual and unexpected features of the present invention, as well as the extreme advantages of the same are:

Contrary to expectation, I have found that with the 3% addition of molybdenum which has a melting point of 2610° C., as compared with palladium which has a melting point of 1554° C. and boron which has a melting point of 2300° C., when combined they give a melting point of the alloy of about 1450° C. or 2600° F. which is far below the melting point of each element of the alloy. This alloy can be made as hard as tempered alloys by increasing the boron in the composition. When I used about 3% boron I found that it would be as hard as tempered steel.

It will be understood that in dental restorations the bulk of the restoration should be nimimal for the patient's comfort and cosmetic appearance. Yet, at the same time, it must have the rigidity and strength to perform the functions of mastication without disturbing the porcelain finish. It has been found that with dental restorations utilizing the present alloy, lightweight, non-bulky restorations can be made which have all of the necessary rigidity and strength to withstand normal mastication and to support without cracking or checking effect on the porcelain adhered thereto, — the porcelain not being required to withstand the strains and stresses of mastication but on the contrary the latter being fully handled by the alloy forming the underlying structure of the restoration.

In my experiments with the use of boron and in contradistinction to the use of oxides to facilitate adhesion of porcelain to a dental alloy, I have found that with the alloy of the present invention which utilizes palladium, boron and molybdenum in the preferred percentages set forth hereinbefore, there are no oxides formed. On the contrary, a small percentage of boron not only acts as a flux and a non-oxidizing element, but it also has the observed advantage that when alloyed with palladium under temperatures of 2600° F. it "sweats" and gravitates to the surface to prevent any oxidation. In this condition boron lends itself completely to a close affinity to the porcelain because it becomes homogeneous with the porcelain fused thereto.

From the foregoing detailed description of the present invention it will be understood that in its broadest aspect the invention provides an alloy of special use in the dental field which consists primarily of palladium and a small percentage of boron which ranges from 1–3%, but preferably 1.3%, and a small percentage of molybdenum of a maximum of 3%. This alloy has a melting point of approximately 2600° F. and is usable as a dental alloy either with or without the application of fusing porcelain.

It will also be understood that the alloy when specially designed for the fusion application of porcelain may have added to it up to but not in excess of 5% nickel which will lower the melting temperature from 2600° F. to about 2500° F. without forming any visible oxides in connection with porcelain adhesion.

What I claim is:

1. A precious metal alloy consisting essentially of, from 1–3% of boron, and a small percentage up to 3% of molybdenum and the balance palladium.

2. A precious metal alloy according to claim 1 wherein the boron content is approximately 1.3% and the molybdenum content is approximately 2%, and the alloy has a melting point of approximately 2600° F.

3. A precious metal alloy according to claim 1 adapted to have porcelain and like ceramics fused thereto which alloy contains a metal selected from the group consisting of nickel and a gallium in an amount of 5% or less.

4. A precious metal alloy according to claim 1 for special use in the dental field and which contains slightly less than 5% of a metal selected from the group consisting of nickel and gallium, and having a melting point of approximately 2500° F. which is particularly adapted to have porcelain fused thereto, said alloy and porcelain having coefficients of expansion which are compatible with each other.

5. A precious metal alloy according to claim 2 for special use in the dental field and which contains slightly less than 5% of a metal selected from the group consisting of nickel and gallium, and having a melting point of approximately 2500° F. which is particularly adapted to have porcelain fused thereto at temperatures approximating 1800° F., said alloy and porcelain having coefficients of expansion which are compatible with each other.

* * * * *